(12) United States Patent
New

(10) Patent No.: US 9,744,125 B2
(45) Date of Patent: *Aug. 29, 2017

(54) USE OF A VIRUCIDAL PREPARATION ON AN AREA OF THE FACE FOR PREVENTION OF TRANSMISSION OR CONTRACTION OF VIRAL ILLNESSES, OR TO SHORTEN THE DURATION OF, OR LESSEN THE SEVERITY OF VIRAL ILLNESSES

(75) Inventor: Kent C. New, Ponte Vedra Beach, FL (US)

(73) Assignee: NUANCE HEALTH, LLC, Ponte Vedra Beach, FL (US)

( * ) Notice: Subject to any disclaimer, the term of this patent is extended or adjusted under 35 U.S.C. 154(b) by 1309 days.

This patent is subject to a terminal disclaimer.

(21) Appl. No.: 12/688,455

(22) Filed: Jan. 15, 2010

(65) Prior Publication Data

US 2011/0178176 A1 Jul. 21, 2011

(51) Int. Cl.
| | |
|---|---|
| *A61K 31/19* | (2006.01) |
| *A61K 31/194* | (2006.01) |
| *A61K 9/00* | (2006.01) |
| *A61K 9/06* | (2006.01) |
| *A61K 47/12* | (2006.01) |

(52) U.S. Cl.
CPC .......... *A61K 9/0043* (2013.01); *A61K 9/0014* (2013.01); *A61K 9/0048* (2013.01); *A61K 9/06* (2013.01); *A61K 47/12* (2013.01)

(58) Field of Classification Search
CPC .... A61K 47/12; A61K 9/0014; A61K 9/0043; A61K 9/0048; A61K 9/06
USPC .................................. 514/557, 558, 561, 574
See application file for complete search history.

(56) References Cited

U.S. PATENT DOCUMENTS

| | | | |
|---|---|---|---|
| 3,297,207 | A | 1/1967 | Ballin |
| 4,897,304 | A | 1/1990 | Hossain et al. |
| 4,975,217 | A | 12/1990 | Brown-Skrobot et al. |
| 6,034,133 | A | 3/2000 | Hendley et al. |
| 6,187,332 | B1 | 2/2001 | Gern et al. |
| 6,210,695 | B1 | 4/2001 | Beerse et al. |
| 6,287,577 | B1 | 9/2001 | Beerse et al. |
| 6,475,501 | B1 | 11/2002 | Kelly et al. |
| 7,045,548 | B2 | 5/2006 | Konowalchuk et al. |
| 2002/0165278 | A1 | 11/2002 | Konowalchuk et al. |
| 2003/0235550 | A1 | 12/2003 | Pan et al. |
| 2005/0260243 | A1 | 11/2005 | Lynch et al. |
| 2005/0271711 | A1 | 12/2005 | Lynch et al. |
| 2008/0267904 | A1* | 10/2008 | Taylor et al. ............... 424/78.37 |
| 2009/0035339 | A1 | 2/2009 | Istvan et al. |
| 2009/0062391 | A1 | 3/2009 | New |
| 2009/0215854 | A1 | 8/2009 | Pan et al. |
| 2009/0247529 | A1 | 10/2009 | Lindahl et al. |

OTHER PUBLICATIONS

Stephenson, Medical News & Perspectives, p. 1163-64, 2004.*
Nyholm et al. Int J of women's Health 2010, 23-35.*
Chloroacetic acid, 2012.*
Lithium Acetate 2012.*
Sigma Aldrich 2012.*
Galasso (NATO, ASI, 143, 1988, 275-298).*
Ellis (Nato ASI 143, 1998, 453-485).*
International Search Report and Written Opinion issued Sep. 21, 2011 in corresponding PCT/US2010/003256.
Howard C. Ansel et al.,"Transdermal Drug Delivery Systems, Ointments, Creams Lotions, and Other Preparations," *Pharmaceutical Dosage Forms and Drug Delivery Systems*, 6th Ed. A Lea Febiger Book, published by Williams & Wilkins (1995) pp. 372-378.
Spector, S.L. "The Common Cold: Current Therapy and Natural History" *J. Allergy Clin. Immunol.* 95:1133-38 (1995).
Lorber, B. "The Common Cold" *J. Gen. Intern. Med.* 11:229-236 (1996).
Gwaltney, JM Jr., et al. "Hand to Hand Transmission of Rhinovirus Colds" *Ann Intern Med* 88(4):463-7 (1978).
Hendley, JO et al. "Evaluation of Virucidal Compounds for Inactivation of Rhinovirus on Hands" *Antimicrob. Agents Chemother.* 14:690-4 (1978).
Poli, G, et al. "Virucidal Activity of Organic Acids" *Food Chem.* (England) 4(4):251-8 (1979).
Hayden, GF et al., "Inactivation of Rhinovirus on Human Fingers by Virucidal Activity of Glutaric Acid" *Antimicrob. Agents. Chemother.* 26(6):928-9 (1984).
Snipes, W. et al, "Inactivation of Lipid-Containing Viruses by Long-Chain Alcohols" *Antimicrob. Agents Chemother.* 11(1):98-104 (1977).
Hayden, GF et al "The Effect of Placebo and Virucidal Paper Handkerchiefs on Viral Contamination of the Hand and Transmission of Experimental Rhinoviral Infection" *J. Infect. Dis.* 152(2):403-7 (1985).

* cited by examiner

*Primary Examiner* — Uma Ramachandran
(74) *Attorney, Agent, or Firm* — Buchanan Ingersoll & Rooney, P.C.

(57) ABSTRACT

A method of reducing or inhibiting the contraction or communication of viral illnesses is proposed. Application of a virucidal preparation containing one or more organic acids (e.g. malic acid) with or without a surfactant (e.g. sodium $C_{14}$-$C_{16}$ olefin sulfonate) in a carrier agent (e.g. petrolatum) to the face of well individuals will reduce the chance that they contract illness with viral illnesses such as viral upper respiratory illnesses, influenza, viral gastroenteritis, viral rhinosinusitis, viral cold sores, and viral conjunctivitis. Application of said ointment to the nares of individuals with a VURI will reduce the chance they transmit the illness by reducing self-contamination of their hands when touching their nose. In addition, individuals suffering from a cold or influenza may reduce the duration or severity of illness by application of the nasal antiviral ointment. The ointment is most effective when applied with a clean applicator two or three times daily.

2 Claims, 6 Drawing Sheets

FIG. 1a Rhinovirus Type 14

| Test Agent* | Initial Load ($Log_{10}TCID_{50}$) | Output Load ($Log_{10}TCID_{50}$) | $Log_{10}$ Reduction |
|---|---|---|---|
| A(2X):B(2X) | 7.58 ± 0.17 | ≤ 3.61 | ≥ 3.97 ± 0.17 |
| A(1X):B(2X) | 7.58 ± 0.17 | ≤ 3.61 | ≥ 3.97 ± 0.17 |
| A(0.2X):B(2X) | 7.58 ± 0.17 | ≤ 3.61 | ≥ 3.97 ± 0.17 |
| A(0X):B(2X) | 7.58 ± 0.17 | 6.96 ± 0.24 | 0.62 ± 0.29 |
| A(2X):B(1X) | 7.58 ± 0.17 | ≤ 3.61 | ≥ 3.97 ± 0.17 |
| A(1X):B(1X) | 7.58 ± 0.17 | ≤ 3.61 | ≥ 3.97 ± 0.17 |
| A(0.2X):B(1X) | 7.58 ± 0.17 | ≤ 3.61 | ≥ 3.97 ± 0.17 |
| A(0X):B(1X) | 7.58 ± 0.17 | 7.33 ± 0.16 | 0.25 ± 0.23 |
| A(2X):B(0.2X) | 7.58 ± 0.17 | ≤ 2.61 | ≥ 4.97 ± 0.17 |
| A(1X):B(0.2X) | 7.58 ± 0.17 | ≤ 2.61 | ≥ 4.97 ± 0.17 |
| A(0.2X):B(0.2X) | 7.58 ± 0.17 | ≤ 2.61 | ≥ 4.97 ± 0.17 |
| A(0X):B(0.2X) | 7.58 ± 0.17 | 7.08 ± 0.19 | 0.50 ± 0.25 |
| A(2X):B(0X) | 7.58 ± 0.17 | ≤ 2.61 | ≥ 4.97 ± 0.17 |
| A(1X):B(0X) | 7.58 ± 0.17 | 2.71 ± 0.12 | 4.87 ± 0.21 |
| A(0.2X):B(0X) | 7.58 ± 0.17 | 4.58 ± 0.17 | 3.00 ± 0.24 |
| A(0X):B(0X) | 7.58 ± 0.17 | 7.21 ± 0.18 | 0.37 ± 0.07 |

* Dilution listed refers to the dilution of each ingredient prior to the 1:1 vol/vol mix. Ingredient A = Malic Acid; Ingredient B = Bioterge.

FIG. 1b Rhinovirus Type 16

| Test Agent* | Initial Load ($Log_{10}TCID_{50}$) | Output Load ($Log_{10}TCID_{50}$) | $Log_{10}$ Reduction |
|---|---|---|---|
| A(2X):B(2X) | 7.83 ± 0.16 | ≤ 3.61 | ≥ 4.22 ± 0.16 |
| A(1X):B(2X) | 7.83 ± 0.16 | ≤ 3.61 | ≥ 4.22 ± 0.16 |
| A(0.2X):B(2X) | 7.83 ± 0.16 | ≤ 3.61 | ≥ 4.22 ± 0.16 |
| A(0X):B(2X) | 7.83 ± 0.16 | 7.58 ± 0.00 | 0.25 ± 0.16 |
| A(2X):B(1X) | 7.83 ± 0.16 | ≤ 3.61 | ≥ 4.22 ± 0.16 |
| A(1X):B(1X) | 7.83 ± 0.16 | ≤ 3.61 | ≥ 4.22 ± 0.16 |
| A(0.2X):B(1X) | 7.83 ± 0.16 | ≤ 3.61 | ≥ 4.22 ± 0.16 |
| A(0X):B(1X) | 7.83 ± 0.16 | 7.58 ± 0.16 | 0.25 ± 0.23 |
| A(2X):B(0.2X) | 7.83 ± 0.16 | ≤ 2.61 | ≥ 5.22 ± 0.16 |
| A(1X):B(0.2X) | 7.83 ± 0.16 | ≤ 2.61 | ≥ 5.22 ± 0.16 |
| A(0.2X):B(0.2X) | 7.83 ± 0.16 | ≤ 2.61 | ≥ 5.22 ± 0.16 |
| A(0X):B(0.2X) | 7.83 ± 0.16 | 6.71 ± 0.12 | 1.12 ± 0.20 |
| A(2X):B(0X) | 7.83 ± 0.16 | ≤ 2.61 | ≥ 5.22 ± 0.16 |
| A(1X):B(0X) | 7.83 ± 0.16 | ≤ 2.61 | ≥ 5.22 ± 0.16 |
| A(0.2X):B(0X) | 7.83 ± 0.16 | ≤ 2.61 | ≥ 5.22 ± 0.16 |
| A(0X):B(0X) | 7.83 ± 0.16 | 7.08 ± 0.19 | 0.75 ± 0.25 |

* Dilution listed refers to the dilution of each ingredient prior to the 1:1 vol/vol mix. Ingredient A = Malic Acid; Ingredient B = Bioterge.

FIG. 2a

| Malic Acid 0.4% (0.2X) : Bioterge 0.1% (0.1X)  (Final Concentration) | | | | | |
|---|---|---|---|---|---|
| Organism | | Initial Load* ($Log_{10}TCID_{50}$) | Output Load ($Log_{10}TCID_{50}$) | $Log_{10}$ Reduction | % Reduction |
| Rhinovirus Type 1B | 1 | 7.97 ± 0.18 | ≤ 2.61 | ≥ 5.36 ± 0.18 | ≥ 99.9996 |
| | 2 | 7.97 ± 0.18 | ≤ 2.61 | ≥ 5.36 ± 0.18 | ≥ 99.9996 |
| Rhinovirus Type 2 | 1 | 6.47 ± 0.17 | ≤ 2.61 | ≥ 3.86 ± 0.17 | ≥ 99.9862 |
| | 2 | 6.47 ± 0.17 | ≤ 2.61 | ≥ 3.86 ± 0.17 | ≥ 99.9862 |
| Rhinovirus Type 14 | 1 | 7.65 ± 0.15 | ≤ 2.61 | ≥ 5.04 ± 0.15 | ≥ 99.9991 |
| | 2 | 7.65 ± 0.15 | ≤ 2.61 | ≥ 5.04 ± 0.15 | ≥ 99.9991 |
| Rhinovirus Type 16 | 1 | 7.77 ± 0.14 | ≤ 2.61 | ≥ 5.16 ± 0.14 | ≥ 99.9993 |
| | 2 | 7.77 ± 0.14 | ≤ 2.61 | ≥ 5.16 ± 0.14 | ≥ 99.9993 |
| Rhinovirus Type 17 | 1 | 7.15 ± 0.21 | ≤ 2.61 | ≥ 4.54 ± 0.21 | ≥ 99.9971 |
| | 2 | 7.15 ± 0.21 | ≤ 2.61 | ≥ 4.54 ± 0.21 | ≥ 99.9971 |
| Rhinovirus Type 10 | 1 | 6.71 ± 0.12 | ≤ 2.61 | ≥ 4.10 ± 0.12 | ≥ 99.9921 |
| | 2 | 6.71 ± 0.12 | ≤ 2.61 | ≥ 4.10 ± 0.12 | ≥ 99.9921 |
| Rhinovirus Type 24 | 1 | 8.35 ± 0.11 | ≤ 2.61 | ≥ 5.74 ± 0.11 | ≥ 99.9998 |
| | 2 | 8.35 ± 0.11 | ≤ 2.61 | ≥ 5.74 ± 0.11 | ≥ 99.9998 |
| Rhinovirus Type 37 | 1 | 6.47 ± 0.11 | ≤ 2.61 | ≥ 3.86 ± 0.11 | ≥ 99.9862 |
| | 2 | 6.47 ± 0.11 | ≤ 2.61 | ≥ 3.86 ± 0.11 | ≥ 99.9862 |
| Rhinovirus Type 26 | 1 | 8.43 ± 0.16 | ≤ 2.61 | ≥ 5.82 ± 0.16 | ≥ 99.9998 |
| | 2 | 8.43 ± 0.16 | ≤ 2.61 | ≥ 5.82 ± 0.16 | ≥ 99.9998 |
| Rhinovirus Type 39 | 1 | 6.97 ± 0.18 | 2.70 ± 0.32 | 4.27 ± 0.37 | 99.9946 |
| | 2 | 6.97 ± 0.18 | ≤ 2.61 | ≥ 4.36 ± 0.18 | ≥ 99.9956 |
| Rhinovirus Type 42 | 1 | 6.40 ± 0.18 | ≤ 2.61 | ≥ 3.79 ± 0.18 | ≥ 99.9838 |
| | 2 | 6.40 ± 0.18 | ≤ 2.61 | ≥ 3.79 ± 0.18 | ≥ 99.9838 |
| Rhinovirus Type 71 | 1 | 6.02 ± 0.20 | ≤ 2.61 | ≥ 3.41 ± 0.20 | ≥ 99.9611 |
| | 2 | 6.02 ± 0.20 | ≤ 2.61 | ≥ 3.41 ± 0.20 | ≥ 99.9611 |
| Rhinovirus Type 79 | 1 | 5.77 ± 0.14 | ≤ 2.61 | ≥ 3.16 ± 0.14 | ≥ 99.9308 |
| | 2 | 5.77 ± 0.14 | ≤ 2.61 | ≥ 3.16 ± 0.14 | ≥ 99.9308 |

* The average virus recovery load from two replicate runs was used as the initial load in each calculation of reduction

FIG. 2b

| Malic Acid 0.4% (0.2X) : Bioterge 0.1% (0.1X)  (Final Concentration) ||||||
|---|---|---|---|---|---|
| Organism | | Initial Load* (Log$_{10}$TCID$_{50}$) | Output Load (Log$_{10}$TCID$_{50}$) | Log$_{10}$ Reduction | % Reduction |
| Rhinovirus Type 83 | 1 | 7.00 ± 0.18 | ≤ 2.61 | ≥ 4.39 ± 0.18 | ≥ 99.9959 |
|  | 2 | 7.00 ± 0.18 | ≤ 2.61 | ≥ 4.39 ± 0.18 | ≥ 99.9959 |
| Rhinovirus Type 84 | 1 | 7.35 ± 0.21 | ≤ 2.61 | ≥ 4.74 ± 0.21 | ≥ 99.9882 |
|  | 2 | 7.35 ± 0.21 | ≤ 2.61 | ≥ 4.74 ± 0.21 | ≥ 99.9882 |
| Adenovirus Type 2 | 1 | 8.52 ± 0.21 | ≤ 2.61 | ≥ 5.91 ± 0.21 | ≥ 99.9999 |
|  | 2 | 8.52 ± 0.21 | ≤ 2.61 | ≥ 5.91 ± 0.21 | ≥ 99.9999 |
| Adenovirus Type 5 | 1 | 8.40 ± 0.23 | 3.58 ± 0.00 | 4.82 ± 0.23 | 99.9985 |
|  | 2 | 8.40 ± 0.23 | 3.80 ± 0.20 | 4.60 ± 0.30 | 99.9975 |
| Adenovirus Type 14 | 1 | 7.60 ± 0.12 | ≤ 2.61 | ≥ 4.99 ± 0.12 | ≥ 99.9990 |
|  | 2 | 7.60 ± 0.12 | ≤ 2.61 | ≥ 4.99 ± 0.12 | ≥ 99.9990 |
| Human Influenza A Virus (H1N1) | 1 | 8.28 ± 0.00 | ≤ 2.61 | ≥ 5.67 ± 0.00 | ≥ 99.9998 |
|  | 2 | 8.28 ± 0.00 | ≤ 2.61 | ≥ 5.67 ± 0.00 | ≥ 99.9998 |
| Human Influenza B Virus | 1 | 8.60 ± 0.20 | ≤ 2.61 | ≥ 5.99 ± 0.20 | ≥ 99.9999 |
|  | 2 | 8.60 ± 0.20 | ≤ 2.61 | ≥ 5.99 ± 0.20 | ≥ 99.9999 |
| Avian Influenza Virus (H9N2) | 1 | 9.28 ± 0.00 | ≤ 2.61 | ≥ 6.67 ± 0.00 | ≥ 99.9898 |
|  | 2 | 9.28 ± 0.00 | ≤ 2.61 | ≥ 6.67 ± 0.00 | ≥ 99.9898 |
| Swine Influenza Virus (H1N1) | 1 | 8.28 ± 0.00 | ≤ 2.61 | ≥ 5.67 ± 0.00 | ≥ 99.9998 |
|  | 2 | 8.28 ± 0.00 | ≤ 2.61 | ≥ 5.67 ± 0.00 | ≥ 99.9998 |
| Human Coronavirus (strain 229E) | 1 | 7.17 ± 0.39 | ≤ 1.61 | ≥ 5.56 ± 0.39 | ≥ 99.9997 |
|  | 2 | 7.17 ± 0.39 | ≤ 1.61 | ≥ 5.56 ± 0.39 | ≥ 99.9997 |
| Parainfluenza Virus Type 3 | 1 | 6.42 ± 0.18 | ≤ 1.61 | ≥ 4.81 ± 0.18 | ≥ 99.9985 |
|  | 2 | 6.42 ± 0.18 | ≤ 1.61 | ≥ 4.81 ± 0.18 | ≥ 99.9985 |
| Respiratory Syncytial Virus | 1 | 5.53 ± 0.25 | ≤ 1.61 | ≥ 3.92 ± 0.25 | ≥ 99.9880 |
|  | 2 | 5.53 ± 0.25 | ≤ 1.61 | ≥ 3.92 ± 0.25 | ≥ 99.9880 |

* The average virus recovery load from two replicate runs was used as the initial load in each calculation of reduction.

FIG. 2c

| Malic Acid 2% (1X) : Bioterge 1% (1X) (Final Concentration) | | | | | |
|---|---|---|---|---|---|
| Organism | | Initial Load* ($Log_{10}TCID_{50}$) | Output Load ($Log_{10}TCID_{50}$) | $Log_{10}$ Reduction | % Reduction |
| Rhinovirus Type 1B | 1 | 7.97 ± 0.18 | ≤ 2.61 | ≥ 5.36 ± 0.18 | ≥ 99.9996 |
| | 2 | 7.97 ± 0.18 | ≤ 2.61 | ≥ 5.36 ± 0.18 | ≥ 99.9996 |
| Rhinovirus Type 2 | 1 | 6.47 ± 0.17 | ≤ 2.61 | ≥ 3.86 ± 0.17 | ≥ 99.9862 |
| | 2 | 6.47 ± 0.17 | ≤ 2.61 | ≥ 3.86 ± 0.17 | ≥ 99.9862 |
| Rhinovirus Type 14 | 1 | 7.65 ± 0.15 | ≤ 2.61 | ≥ 5.04 ± 0.15 | ≥ 99.9991 |
| | 2 | 7.65 ± 0.15 | ≤ 2.61 | ≥ 5.04 ± 0.15 | ≥ 99.9991 |
| Rhinovirus Type 16 | 1 | 7.77 ± 0.14 | ≤ 2.61 | ≥ 5.16 ± 0.14 | ≥ 99.9993 |
| | 2 | 7.77 ± 0.14 | ≤ 2.61 | ≥ 5.16 ± 0.14 | ≥ 99.9993 |
| Rhinovirus Type 17 | 1 | 7.15 ± 0.21 | ≤ 2.61 | ≥ 4.54 ± 0.21 | ≥ 99.9971 |
| | 2 | 7.15 ± 0.21 | ≤ 2.61 | ≥ 4.54 ± 0.21 | ≥ 99.9971 |
| Rhinovirus Type 10 | 1 | 6.71 ± 0.12 | ≤ 2.61 | ≥ 4.10 ± 0.12 | ≥ 99.9921 |
| | 2 | 6.71 ± 0.12 | ≤ 2.61 | ≥ 4.10 ± 0.12 | ≥ 99.9921 |
| Rhinovirus Type 24 | 1 | 8.35 ± 0.11 | ≤ 2.61 | ≥ 5.74 ± 0.11 | ≥ 99.9998 |
| | 2 | 8.35 ± 0.11 | ≤ 2.61 | ≥ 5.74 ± 0.11 | ≥ 99.9998 |
| Rhinovirus Type 37 | 1 | 6.47 ± 0.11 | ≤ 2.61 | ≥ 3.86 ± 0.11 | ≥ 99.9862 |
| | 2 | 6.47 ± 0.11 | ≤ 2.61 | ≥ 3.86 ± 0.11 | ≥ 99.9862 |
| Rhinovirus Type 26 | 1 | 8.43 ± 0.16 | ≤ 2.61 | ≥ 5.82 ± 0.16 | ≥ 99.9998 |
| | 2 | 8.43 ± 0.16 | ≤ 2.61 | ≥ 5.82 ± 0.16 | ≥ 99.9998 |
| Rhinovirus Type 39 | 1 | 6.97 ± 0.18 | ≤ 2.61 | ≥ 4.36 ± 0.18 | ≥ 99.9956 |
| | 2 | 6.97 ± 0.18 | ≤ 2.61 | ≥ 4.36 ± 0.18 | ≥ 99.9956 |
| Rhinovirus Type 42 | 1 | 6.40 ± 0.18 | ≤ 2.61 | ≥ 3.79 ± 0.18 | ≥ 99.9938 |
| | 2 | 6.40 ± 0.18 | ≤ 2.61 | ≥ 3.79 ± 0.18 | ≥ 99.9938 |
| Rhinovirus Type 71 | 1 | 6.02 ± 0.20 | ≤ 2.61 | ≥ 3.41 ± 0.20 | ≥ 99.9611 |
| | 2 | 6.02 ± 0.20 | ≤ 2.61 | ≥ 3.41 ± 0.20 | ≥ 99.9611 |
| Rhinovirus Type 79 | 1 | 5.77 ± 0.14 | ≤ 2.61 | ≥ 3.16 ± 0.14 | ≥ 99.9308 |
| | 2 | 5.77 ± 0.14 | ≤ 2.61 | ≥ 3.16 ± 0.14 | ≥ 99.9308 |

* The average virus recovery load from two replicate runs was used as the initial load in each calculation of reduction.

FIG. 2d

| Malic Acid 2% (1X) : Bioterge 1% (1X)  (Final Concentration) | | | | | |
|---|---|---|---|---|---|
| Organism | | Initial Load* ($Log_{10}TCID_{50}$) | Output Load ($Log_{10}TCID_{50}$) | $Log_{10}$ Reduction | % Reduction |
| Rhinovirus Type 83 | 1 | 7.00 ± 0.18 | ≤ 2.61 | ≥ 4.39 ± 0.18 | ≥ 99.9959 |
| | 2 | 7.00 ± 0.18 | ≤ 2.61 | ≥ 4.39 ± 0.18 | ≥ 99.9959 |
| Rhinovirus Type 84 | 1 | 7.35 ± 0.21 | ≤ 2.61 | ≥ 4.74 ± 0.21 | ≥ 99.9982 |
| | 2 | 7.35 ± 0.21 | ≤ 2.61 | ≥ 4.74 ± 0.21 | ≥ 99.9982 |
| Adenovirus Type 2 | 1 | 8.52 ± 0.21 | ≤ 2.61 | ≥ 5.91 ± 0.21 | ≥ 99.9999 |
| | 2 | 8.52 ± 0.21 | ≤ 2.61 | ≥ 5.91 ± 0.21 | ≥ 99.9999 |
| Adenovirus Type 5 | 1 | 8.40 ± 0.23 | ≤ 2.61 | ≥ 5.79 ± 0.23 | ≥ 99.9998 |
| | 2 | 8.40 ± 0.23 | ≤ 2.61 | ≥ 5.79 ± 0.23 | ≥ 99.9998 |
| Adenovirus Type 14 | 1 | 7.60 ± 0.12 | ≤ 2.61 | ≥ 4.99 ± 0.12 | ≥ 99.9990 |
| | 2 | 7.60 ± 0.12 | ≤ 2.61 | ≥ 4.99 ± 0.12 | ≥ 99.9990 |
| Human Influenza A Virus (H1N1) | 1 | 8.28 ± 0.00 | ≤ 3.61 | ≥ 4.67 ± 0.00 | ≥ 99.9979 |
| | 2 | 8.28 ± 0.00 | ≤ 3.61 | ≥ 4.67 ± 0.00 | ≥ 99.9979 |
| Human Influenza B Virus | 1 | 8.60 ± 0.20 | ≤ 3.61 | ≥ 4.99 ± 0.20 | ≥ 99.9990 |
| | 2 | 8.60 ± 0.20 | ≤ 3.61 | ≥ 4.99 ± 0.20 | ≥ 99.9990 |
| Avian Influenza virus (H9N2) | 1 | 9.28 ± 0.00 | ≤ 3.61 | ≥ 5.67 ± 0.00 | ≥ 99.9998 |
| | 2 | 9.28 ± 0.00 | ≤ 3.61 | ≥ 5.67 ± 0.00 | ≥ 99.9998 |
| Swine Influenza virus (H1N1) | 1 | 8.28 ± 0.00 | ≤ 3.61 | ≥ 4.67 ± 0.00 | ≥ 99.9979 |
| | 2 | 8.28 ± 0.00 | ≤ 3.61 | ≥ 4.67 ± 0.00 | ≥ 99.9979 |
| Human Coronavirus (strain 229E) | 1 | 7.17 ± 0.39 | ≤ 1.58 | ≥ 5.59 ± 0.39 | ≥ 99.9997 |
| | 2 | 7.17 ± 0.39 | ≤ 1.58 | ≥ 5.59 ± 0.39 | ≥ 99.9997 |
| Parainfluenza Virus Type 3 | 1 | 6.42 ± 0.18 | ≤ 2.61 | ≥ 3.81 ± 0.18 | ≥ 99.9845 |
| | 2 | 6.42 ± 0.18 | ≤ 2.61 | ≥ 3.81 ± 0.18 | ≥ 99.9845 |
| Respiratory Syncytial Virus | 1 | 5.53 ± 0.25 | ≤ 1.58 | ≥ 3.95 ± 0.25 | ≥ 99.9888 |
| | 2 | 5.53 ± 0.25 | ≤ 1.58 | ≥ 3.95 ± 0.25 | ≥ 99.9888 |

* The average virus recovery load from two replicate runs was used as the initial load in each calculation of reduction.

USE OF A VIRUCIDAL PREPARATION ON AN AREA OF THE FACE FOR PREVENTION OF TRANSMISSION OR CONTRACTION OF VIRAL ILLNESSES, OR TO SHORTEN THE DURATION OF, OR LESSEN THE SEVERITY OF VIRAL ILLNESSES

CROSS-REFERENCE TO RELATED APPLICATIONS

Not Applicable

STATEMENT REGARDING FEDERALLY SPONSORED RESEARCH OR DEVELOPMENT

No federally sponsored research was used in the development of this invention.

REFERENCE TO SEQUENCE LISTING, A TABLE, OR A COMPACT DISC APPENDIX

Not applicable.

BACKGROUND OF THE INVENTION

1. Field of the Invention

Embodiments of this disclosure relate to virucidal compositions for the prevention of the spread of viral illnesses, and/or to shorten the duration of and/or severity of viral illnesses such as viral upper respiratory infections (VURI, including the "common cold" and the "flu"). Preferred embodiments of this disclosure relate to the use of a virucidal preparation on an area of the face of uninfected individuals to reduce the chance that they contract a viral illness. Embodiments of this disclosure also relate to preparations and the use thereof on an area of the face of infected individuals to reduce the severity and/or duration of viral illness.

The spread of viral illnesses such at VURI frequently occur through hand-to-hand transmission of virus followed by self-contamination with virus of the nasal, oral or conjunctival mucosa. Typically, an individual with a VURI will either directly or indirectly contaminate the hands of another individual who does not have the illness. The uninfected individual will thereby have viral particles on their hands. These viral particles initiate infection after the individual contaminates their own nasal, oral or conjunctival mucosa with the viral particles on their hands. In this way, although transmission occurs through the initial step of hand-to-hand transfer of viral particles, infection of new individuals typically occurs only if active viral particles gain access to the mucosa. Such access typically occurs via the face. More specifically, such access typically occurs via the mucous membranes of the face, such as the nasal, oral or conjunctival mucous membranes.

Knowledge of the primary causative agents and the mechanism of transmission of viral illnesses have been in the public domain for over twenty years. Although considerable progress has been made in understanding the molecular biology of viruses responsible for these illnesses, little progress has been made in the prevention or treatment of viral illnesses. Efforts aimed at reducing transmission of viral illnesses have focused on developing products for use on the hands. These efforts fail largely due to two reasons: 1, the viruses responsible for VURI and other viral illnesses are difficult to inactivate; and 2, it is nearly impossible to keep one's hands free of viral contamination because they repeatedly come in contact with contaminated objects.

Certain embodiments of this disclosure aim to significantly reduce the spread of viral illnesses. Embodiments of this disclosure rely on the application of a broadly effective virucidal preparation to areas of the face including the entrance to the nostrils (the nares), the lips, and/or the conjunctiva of the eyes.

2. Description of the Prior Art

The art in the prevention of transmission of VURI and other viral illnesses is extensive, but it has heretofore focused primarily on the inactivation of viral particles on the hands. Previous work lends insight into potential effective agents for use in this disclosure.

Hendley et al. investigated the antiviral activity of several compounds including iodine, ethyl alcohol, benzalkonium chloride (BAK), and hexachlorophene. These agents were known for their anti-bacterial activity, but all except iodine performed poorly as antiviral agents. Unfortunately iodine is too irritating to the skin to be frequently applied.

Poli et al. investigated the antiviral activity of several organic acids such as citric, malic, pyruvic, and succinic acids and found them to be effective against herpes simplex virus, rhabdovirus, and other enveloped viruses, but not effective against adenovirus, the only naked virus tested. Hayden, et al. reported that hand lotions containing 2% glutaric acid were more effective than placebo at inactivating certain serotypes of rhinovirus. Rhinoviruses are responsible for more colds than any other virus family, but not all colds. Therefore the use of organic acids alone as an antiviral agent will likely have some effectiveness at reducing the transmission of common cold viruses, but will not offer comprehensive protection against colds or other viral illnesses.

Snipes, et al. discovered that alcohols of certain chain lengths were effective at inactivating lipid-containing viruses. Unfortunately, the alcohols found most effective are extremely insoluble in aqueous media, making them somewhat difficult to employ in practical applications. However, further work with alcohols has lead to other useful antiviral inventions by Hendley, et al. and Konowalchuk, et al., described below.

Hendley, et al. (U.S. Pat. No. 6,034,133) disclose a virucidal hand lotion containing malic acid, citric acid, and a C1 to C6 alcohol which effectively inactivates rhinovirus contamination of treated hands. Their work also revealed that the use of lotions containing malic acid and citric acid without an alcohol would reduce, but not eliminate rhinovirus contamination of treated hands.

Recently, Konowalchuk, et al. (U.S. Pat. No. 7,045,548) disclose a method of inactivating viruses with a composition of a C1 to C3 monohydroxy alcohol or a C2 to C4 diol with a sufficient amount of an acid (either organic or inorganic) to adjust the pH of the composition to below 4.6. This is demonstrated effective in topically treating lesions caused by herpes simplex virus. It is also proposed that the composition may be effective at ameliorating the symptoms of a common cold with intranasal application. No mention is made of the use of the composition on an area of the face to prevent access for active viral particles to mucosal membranes to reduce transmission of or severity and duration of viral illnesses.

Brown-Skrobot, et al. (U.S. Pat. No. 4,975,217) disclose a method of inactivating viruses and bacteria through the application of a combination of an organic acid and an anionic surfactant, with or without an alcohol to the hands. This work describes the finding that a combination of an organic acid with an anionic surfactant has antiviral activity against both enveloped and naked viruses, thus is effective against a broad array of viruses able to cause VURI. The composition is described as a virucidal lotion for the hands.

Hossain, et al. (U.S. Pat. No. 4,897,304) disclose the use of a combination of organic acids and a surfactant in a facial tissue to reduce the spread of viruses which cause VURI. However, Hayden, et al. reported that the use of facial tissues can interrupt the transmission of viruses whether treated with the antiviral composition or not. Hence no distinct advantage in reducing transmission of viruses which cause VURI is obtained by this product.

In summary, prior art contains several examples of various antiviral compositions for use on the hands to reduce transmission of viruses that cause VURI. Some of these references also disclose use of antiviral compositions in the nasal passages to ameliorate the symptoms of a VURI. No prior disclosure describes the use of an antiviral composition on an area of the face of individuals to reduce or stop access for active viral particles to mucous membranes, or in the eyes of individuals, to reduce or inhibit transmission or contraction of viral illnesses.

BRIEF SUMMARY OF THE INVENTION

Embodiments of this disclosure include virucidal preparations for and methods of:
  reducing or inhibiting transmission of a viral illness to a user;
  reducing or inhibiting transmission of a viral illness from a user;
  reducing or inhibiting contraction of a viral illness;
  shortening the duration of a viral illness; and
  lessening the severity of a viral illness.
Reducing, as used in this disclosure, means decreasing the likelihood of something occurring. Inhibiting, as used in this disclosure, means stopping something from occurring.

As opposed to the plethora of products which attempt to keep hands free of viral contaminant, a goal of embodiments of this disclosure aims at inactivating virus on the face. For example, embodiments of this disclosure include applying a preparation on an area of the face. Preferred embodiments of this disclosure include reducing or inhibiting access for active viral particles to mucous membranes, such as oral, nasal or conjunctival mucous membranes. Preferred embodiments of this disclosure include application on entry areas to such mucous membranes. For example, embodiments include applying a preparation on the nares, lips or skin surrounding the eye, such as the eye lid or skin below the eye (i.e., eye bag). Preferred embodiments of this disclosure also include application on the conjunctiva, generally via an eye drop.

Nares, as used in this disclosure, refer to the skin at the entrance to the nostril. The nasal mucous membranes are not considered part of the nares, though application of a preparation to the nares may result in application to a small part of the nasal mucous membranes.

Lips, as used in this disclosure, refer to the visible body part at the mouth of humans and many animals. Lips are soft, movable, and serve as the opening for food intake and in the articulation of sound and speech. The oral mucous membranes are generally not considered part of the lips, though application of a preparation to the lips will often result in application to at least a small part of the oral mucous membranes. Moreover, the transition from the lips to the oral mucous membrane of a human is often gradual and difficult to determine.

Since contraction of VURI and other viral illnesses frequently occurs following contamination of the nasal mucosa with virus, preferred embodiments of this disclosure are effective at reducing contraction and/or transmission of a variety of viral illnesses. As preferred ingredients of preparations of this disclosure have broad anti-viral activity, use of embodiments of antiviral preparations of this disclosure have potential effectiveness against many antiviral illnesses including the common cold, influenza, herpes simplex virus (HSV) cold sores, viral gastroenteritis, roseola, viral conjunctivitis, and viral rhinosinusitis. Preferred embodiments of antiviral preparations of this disclosure are effective against viral upper respiratory infections (VURI). A VURI, as used in this disclosure includes, but is not necessarily limited to, infection with rhinovirus, adenovirus, influenza virus (e.g., Human A & B, Avian H9N2, and Swine H1N1), Human Coronavirus, Parainfluenza, Picornavirus, and Respiratory Syncytial Virus.

Embodiments of the virucidal preparation may contain a mixture of organic acids, with or without a surfactant in a carrier appropriate for delivery of the antiviral composition to the target region of the face. The virucidal preparation may be used in well individuals to reduce the chance that they will contract a viral illness. The preparation may also be used by individuals with a viral illness to reduce the duration and severity of illness. The preparation may also be used by individuals with a viral illness to reduce the chance they transmit the viral illness.

Appropriate embodiments of this disclosure are described herein; however the description of these embodiments is not intended to limit the scope of the invention. For application to the nares, the antiviral composition may be prepared in appropriate carrier agents such as petrolatum, glycerin, mineral oil, dipropylene glycol, eucalyptus oil, dissolving creams, and xanthan gum. Appropriate pH for effective anti-viral preparations may be between 4 and 8. The topical agent is expected to remain on the skin for approximately 30 minutes or longer.

For application to the lips, the antiviral composition may be prepared in dissolving creams, beeswax, and other carrier agents or balms. Appropriate pH for effective anti-viral lip preparations may be between 4 and 7. The topical agent is expected to remain on the lips for approximately 10 minutes or longer.

For application as an ophthalmic preparation, the antiviral composition may be prepared in a saline solution. Appropriate salts for such preparations include, but are not limited to phosphate, potassium chloride, sodium chloride. The appropriate pH for an effective anti-viral ophthalmologic preparation may be between 4 and 8.

This disclosure also includes the development of appropriate applicators to assist in delivering the anti-viral preparation on an area of the face. Preferred embodiments include a small tube with a dome or beveled tip for application to the nares or the lips. The dome tip can have a single, centrally located hole or multiple peripherally located holes for extrusion of the ointment. For ophthalmic use, the preparation would typically be provided in an aqueous solution provided in a container appropriate to allow for eye drop application. This disclosure also includes kits containing both an applicator of the types discussed above and an anti-viral preparation.

BRIEF DESCRIPTION OF THE SEVERAL VIEWS OF THE DRAWING

The disclosure will be described in greater detail in the following by way of example only with reference to various non-limiting embodiments as depicted in the annexed figures.

FIGS. 1a-b show dilution testing results for malic acid and sodium $C_{14}$-$C_{16}$ olefin sulfonate (Bio-Terge®). FIG. 1a demonstrates in vitro testing results for listed dilutions of test agent exposed to Rhinovirus Type 14 for 60 seconds. FIG. 1b demonstrates in vitro testing results for listed dilutions of test agent exposed to Rhinovirus Type 16 for 60 seconds. The table lists input titer, output titer and calculated log reduction in viral titer for each dilution.

FIGS. 2a-d show in vitro viral testing results for malic acid and sodium $C_{14}$-$C_{16}$ olefin sulfonate at two different concentrations (2a and b represent 0.4%/0.1%, 2c and d represent 2%/1%). Both test agents were investigated for antiviral activity against a panel of 25 viruses as listed. Exposure time of test agent to virus was 60 seconds.

DETAILED DESCRIPTION OF THE INVENTION

Embodiments of this disclosure describe a powerful combination of agents which has the relatively uncommon property of being safe and tolerable on the skin as well as possessing broad highly efficacious antiviral activity. Potential applications of this topical antiviral preparation are numerous. Embodiments of this disclosure detail the use of the preparation on at least one area the face for purposes including reduction of transmission and duration and severity of viral illnesses. For example, using the topical antiviral preparation on the nares will reduce the transmission or contraction of the common cold or influenza.

Embodiments of this disclosure described may be used in well individuals to reduce the chance that they will contract a viral illness. Alternatively, embodiments may be utilized in infected individuals to reduce the chance they contaminate their hands with virus when touching their face, thereby reducing the chance they spread the illness. Use of an embodiment of the virucidal preparation immediately following contraction of a cold has resulted in shortening the duration and lessening the severity of illness. This finding suggests embodiments may be utilized to reduce severity and duration of viral illnesses Embodiments of this disclosure are described below with preferred embodiments; however it should be understood that it is not intended to limit the invention to the embodiments described. The invention is intended to include all alternatives as may be included within the spirit and scope of the invention as defined by the appended claims.

Organic acids which are effective against viruses and are therefore appropriate for use in this disclosure include: valeric acid, lactic acid, glycolic acid, pelargonic acid, aspartic acid, malic acid, and citric acid. Appropriate embodiments of this disclosure include any combination of one or more of these organic acids. One embodiment is malic acid (2% w/v) plus citric acid (2% w/v) in an appropriate carrier agent. This combination of acids has been demonstrated effective against certain serotypes of rhinovirus. Said ointment would be applied either directly using a finger, or indirectly using an applicator to the nares one or more times per day. Ideally the ointment is to be applied to the nares using a clean applicator several times daily.

The preparation or ointment may comprise, consist essentially of or consist of up to 10% w/v of each organic acid, preferably 0.1-5% w/v. A preparation or ointment that consists essentially of at least one organic acid and a carrier is limited to the at least one organic acid as the only virucidal agent. This ointment can be produced by making concentrated solutions of the desired acids in water and then diluting in the carrier to the appropriate desired final concentration. Potential carriers include: petrolatum, glycerin, mineral oil, dipropylene glycol, eucalyptus oil, xanthan gum, and other non-toxic gels, creams, or ointments.

Organic acids alone have been demonstrated to effectively inactivate only some rhinovirus serotypes, and are ineffective at inactivating adenovirus. However, the combination of organic acids and a surfactant, particularly alkyl sulfonates, has shown effectiveness at inactivating viruses from several families including: rhinovirus, adenovirus, influenza virus, and parainfluenza virus. Members of these virus families are responsible for a majority of common colds and the flu in adults. Therefore, a more effective embodiment comprises, consists essentially of, or consists of a combination of one or more organic acids and one or more surfactants. A preparation or ointment that consists essentially of at least one organic acid, a surfactant and a carrier is limited to the at least one organic acid and surfactant as the only virucidal agents.

An independent microbiology laboratory has performed extensive in vitro testing of the combination of malic acid and sodium $C_{14}$-$C_{16}$ olefin sulfonate (Bio-Terge®) against several viruses. Clinical testing determined that malic acid 2% and Bio-Terge® 1% is very tolerable when applied to the skin of the face including the nares up to six times daily. In vitro testing was then performed of serial dilutions of each ingredient starting with the maximum concentration of malic acid 2%/Bio-Terge® 1%. The dilution testing revealed that malic acid 0.4%/Bio-Terge® 0.1% resulted in greater than 3 log reduction in virus titer of two serotypes of Rhinovirus; equal to the antiviral efficacy of the maximum concentration preparation tested. The dilution testing results are shown in FIGS. 1a and 1b. FIG. 1a shows dilution testing results obtained with malic acid and Bio-Terge®, the dilutions tested against Rhinovirus Type 14. FIG. 1b shows dilution testing results obtained with malic acid and Bio-Terge®, the dilutions tested against Rhinovirus Type 16.

Following dilution testing, further in vitro testing was performed to evaluate the efficacy of two formulations (malic acid 2%/Bio-Terge® 1% and malic acid 0.4%/Bio-Terge® 0.1%) against a wide spectrum of viruses. Specifically, the formulations were tested against 15 serotypes of Rhinovirus, 3 serotypes of Adenovirus (2, 5, and 14), 4 strains of Influenza virus (Human A & B, Avian H9N2, and Swine H1N1), Human Coronavirus strain 229E, Parainfluenza virus type 3, and Respiratory Syncytial Virus. Both formulations demonstrated greater than 3 log reduction in titer of all 25 viruses tested and greater than 4 log reduction in 18 of 25 viruses (including all four influenza viruses) with a 60 second exposure time. The viral testing results are shown in FIGS. 2a-d.

A preparation or ointment may comprise, consist essentially of, or consist of up to 2% w/v malic acid and 1% w/v Bio-Terge®, preferably up to 1% w/v malic acid and 0.5% w/v Bio-Terge®, more preferably up to 0.4% w/v malic acid and 0.1% w/v Bio-Terge®.

Preliminary clinical research demonstrated safety and tolerability of the topical antiviral preparation. In addition, the preliminary clinical research has demonstrated effectiveness at reducing frequency of VURI illness. Further, use of the ointment, at least by application to the nares, has demonstrated effectiveness at reducing the duration and severity of VURI illness, and has demonstrated effectiveness against influenza as well as other viral illnesses such as viral gastroenteritis.

Other surfactants with demonstrated effectiveness at inactivating viruses when combined with organic acids, and thus are suitable for this disclosure include: sodium dodecyl benzene sulfonate (BIOSOFT D-35X), sodium dodecyl sulfate (SDS), sodium lauryl sulfate (SLS), and sodium dioctyl sulfosuccinate (AEROSOL® OT). Appropriate concentration of the organic acid is 0.1-10% w/v, and of the surfactant is 0.1-10% v/v. Most effective and non-irritating embodiments include the organic acid at 0.1-5% w/v and the surfactant at 0.1-2% v/v.

Appropriate embodiments of this disclosure include any combination of one or more of the organic acids listed above with one of the surfactants listed in an appropriate carrier agent. The appropriate carrier agent for embodiments of this disclosure depends on the target region of the face. For the nares, preparing the active ingredients in an ointment allows for ease of application and persistence. For the lips, a more appropriate carrier would be beeswax or similar agent suitable to apply as a lip balm. Alternatively, the formulation could be prepared in a dissolving cream so that it can be applied to the lips, nares, or any portion of the face prior to the application of make-up.

Appropriate viscosity for skin preparations at 25° C. may be at least 10 P, or at least 25 P, or at least 50 P, or at least 200 P, or at least 1000 P.

As viral illnesses can also be contracted in or through the eyes, it is an appropriate embodiment of this disclosure is to prepare the active ingredients in normal saline or other appropriate solution for application to the conjunctiva. Such a preparation would be appropriate for the prevention of contraction of VURI as well as viral conjunctivitis.

In embodiments of the disclosure, the preparation may be applied to at least one area of the face, such as the lips, nares or conjunctiva, one or more times a day. Such application may be for prevention of contraction of influenza. Preferably, the application is at least once every 8 hours, at least one every 6 hours, at least once every 4 hours, or at least once every 2 hours.

While the present invention has been described with reference to various embodiments, it is to be understood that the invention is not limited to the disclosed embodiments. To the contrary, the invention is intended to cover various modifications and equivalent arrangements included within the spirit and scope of the appended claims.

The invention claimed is:

1. A method of reducing the chance of contraction or transmission of a viral upper respiratory illness, said method comprising:

applying a virucidal preparation to the conjunctiva, and reducing the chance of contraction or transmission of a viral upper respiratory illness, the preparation comprising an antiviral agent, which is the only active antiviral agent, and one or more carrier agents, wherein the virucidal preparation further comprises one or more surfactants, wherein the antiviral agent consists of one or more organic acids, wherein at least one organic acid is malic acid, wherein the malic acid is at a concentration of up to 2% w/v, wherein the carrier agent is suitable for application to the eyes, and wherein the virucidal preparation is applied to the eyes one or more times a day.

2. The method of claim 1, wherein the preparation consists of malic acid, one or more carrier agents, and one or more surfactants.

* * * * *